(12) United States Patent
Novotny

(10) Patent No.: US 7,479,283 B1
(45) Date of Patent: Jan. 20, 2009

(54) **ACELLULAR *PERTUSSIS* VACCINE COMPRISING A COMBINATION OF THE 69 KDA AND THE FILAMENTOUS HAEMAGGLUTININ ANTIGENS OF *BORDETELLA PERTUSSIS***

(75) Inventor: Pavel Novotny, Beckenham (GB)

(73) Assignee: UCB Pharma Limited, Slough, Berkshire (GB)

( * ) Notice: Subject to any disclaimer, the term of this patent is extended or adjusted under 35 U.S.C. 154(b) by 0 days.

(21) Appl. No.: 08/450,336

(22) Filed: May 25, 1995

Related U.S. Application Data

(63) Continuation of application No. 08/221,451, filed on Apr. 1, 1994, now abandoned, which is a continuation of application No. 08/137,778, filed on Oct. 19, 1993, now abandoned, which is a continuation of application No. 07/773,649, filed on Oct. 17, 1991, now abandoned.

(30) Foreign Application Priority Data

May 8, 1989 (GB) .................................. 8910570.4
Apr. 26, 1990 (WO) ..................... PCT/GB90/00649

(51) Int. Cl.
*A61K 39/10* (2006.01)
*A61K 39/02* (2006.01)
*A61K 39/00* (2006.01)

(52) U.S. Cl. .............. 424/253.1; 424/240.1; 424/234.1; 424/242.1; 424/184.1; 514/2

(58) Field of Classification Search .............. 424/253.1, 424/254.1, 240.1, 234.1, 184.1, 242.1; 514/2
See application file for complete search history.

(56) References Cited

U.S. PATENT DOCUMENTS

| | | | | |
|---|---|---|---|---|
| 4,455,297 | A | | 6/1984 | Syukuda et al. |
| 4,997,915 | A | * | 3/1991 | Tan et al. ..................... 530/396 |
| 5,101,014 | A | * | 3/1992 | Burns et al. .................. 530/350 |
| 5,162,223 | A | * | 11/1992 | Brennan et al. ........ 435/240.26 |
| 5,237,052 | A | * | 8/1993 | Novotny ..................... 530/350 |
| 5,276,142 | A | * | 1/1994 | Gotto ......................... 530/413 |
| 5,358,868 | A | * | 10/1994 | Klein et al. ................ 435/69.1 |
| 5,438,120 | A | | 8/1995 | Novotny |
| 5,444,159 | A | | 8/1995 | Jackson |
| 5,648,080 | A | * | 7/1997 | Novotny .................. 424/254.1 |
| 5,667,787 | A | | 9/1997 | Jackson |
| 5,885,586 | A | | 3/1999 | Eckhardt et al. |
| 5,885,587 | A | | 3/1999 | Eckhardt et al. |
| 5,895,655 | A | | 4/1999 | Eckhardt |
| 5,897,867 | A | | 4/1999 | Eckhardt |
| 5,972,225 | A | * | 10/1999 | Karras et al. ................ 210/694 |
| 6,048,700 | A | | 4/2000 | Novotny |
| 6,051,240 | A | | 4/2000 | Suehara et al. ........... 424/240.1 |
| 6,127,151 | A | | 10/2000 | Novotny |
| 6,210,685 | B1 | | 4/2001 | Novotny |

FOREIGN PATENT DOCUMENTS

| | | | |
|---|---|---|---|
| EP | 0 043 349 | A1 | 1/1982 |
| EP | 0 162 639 | A3 | 5/1985 |
| EP | 0 162 639 | | 11/1985 |
| EP | 0175841 | * | 4/1986 |
| EP | 0 235 474 | | 8/1987 |
| EP | 0231083 | * | 8/1987 |
| EP | 0 235 474 | | 9/1987 |
| EP | 0 267 998 | | 5/1988 |
| EP | 0 267 998 | A1 | 5/1988 |
| EP | 0267498 | * | 5/1988 |
| EP | 0267998 | * | 5/1988 |
| EP | 0 272 174 | | 6/1988 |
| EP | 0 336 736 | A1 | 10/1989 |
| EP | 0 437 687 | A2 | 7/1991 |
| EP | 0 462 534 | A2 | 12/1991 |
| EP | 0462534 | A2 * | 12/1991 |
| EP | 0 471 726 | B1 | 2/1992 |
| EP | 0 527 753 | B1 | 2/1993 |
| EP | 0 747 058 | A1 | 12/1996 |
| FR | 2 606 789 | | 5/1988 |
| WO | WO 90/13313 | | 11/1990 |
| WO | WO 91/15505 | | 10/1991 |
| WO | WO 91/15571 | | 10/1991 |

OTHER PUBLICATIONS

Novotny et al The Journal of Infectious Dis 164:111-22;1991.*
De Magistris et al, J. Exp Med 168:1351-1392 1988.*
Thomas et al J. of Infect Dis 159:211-2418, 1989.*
Redhead et al, Infect & Immunity 44:724-729, 1984 (Abst).*
Tagliabue et al Tokai J. Exp Clin Med vol. 13 pp. 253-257, 1988.*
Robinson et al. Infect. Immun. 40: 523-528, 1983.*

(Continued)

*Primary Examiner*—S. Devi
(74) *Attorney, Agent, or Firm*—Millen, White, Zelano & Branigan, P.C.

(57) ABSTRACT

An acellular vaccine is provided which in use provides protection against *Bordetella pertussis* infections. The vaccine is based on the synergistic combination of two antigenes from *B. pertussis*, the 69 kDa, and the filamentous haemagglutinin antigens.

30 Claims, 3 Drawing Sheets

OTHER PUBLICATIONS

Shahin et al. J. Exp. Med. 171: 63-73, 1990.*
Chozono et al. J. Biol. Stand. 16(2): 83-89, 1988.*
Sato et al. In: Robbins et al. (Ed.), Bacterial Vaccines, Praeger, New York, pp. 349-357, 1987.*
Novotny et al. Dev. Biol. Stand. 61: 27-41, 1985.*
Rappuoli et al. Vaccine 10(14): 1027-1032, 1992.*
Kimura et al. Acta Pediatr. Jpn. 30: 143-153, 1988.*
Gotto et al. In: International Workshop on *Bordetella pertussis,* Aug. 18-20, Rocky Mountain Laboratories, Hamilton, Montana, 1988.*
Robinson et al. In: Pathogenesis and Immunity in *Pertussis,* (Ed) AC Wardlaw et al., John Wiley & Sons Ltd., Chapter 19, pp. 399-417, 1988.*
Sato et al. Lancet 1: 122-126, 1984.*
Sato et al. In: Bacterial Vaccines and Local Immunity, Proceedings of Sclaco International Conference, Siena, Italy, Nov. 17-19, pp. 191-197, 1986.*
Thomas et al. J. Infect. Dis. 159: 211-218, Feb. 1989.*
Ibsen et al. Vaccine 11: 318-322, 1993.*
Weiss et al. Infect. Immun. 57: 2674-2682, Sep. 1989.*
Sato et al. Infect. Immun. 46: 415-421, 1984.*
Kimura et al. Infect. Immun. 58: 7-16, 1990, abstract.*
Robinson et al. Dev. Biol. Stand. 61: 165-172, 1985.*
Robinson et al. FEMS Microbiol. Lett. 1o: 241-244, 1981.*
Ashworth et al. Lancet 2: 878-881, 1983.*
Cahill et al. Vaccine 13: 455-462, 1995.*
Sato et al. Tokai J. Exp. Clin. Med. 13 Suppl. 79-88, 1988.*
Preston et al. J. Med. Microbiol. 32: 63-68, 1990.*
De Magistris et al J. Exp Med 168:1351-1362 Oct. 1988 Dissecting Human T Cell Response Against *Bordetella* species.*
Thomas et al The J. of Inf Dis 159: 211-218 Feb. 1959 Human Serum Antibody Responses to *Bordetella pertussis* Infection & *pertussis* Vaccination.*
Brennan et al I & T 56: 3159-3195 Identification of a 69-Kd Nonfimbrial Protein as an Agglutinogen of *B pertussis.* *
Redhead Infect Immunity 44: 724-729 1984 (Abstract Only).*
Berenbaum MC. Clin. Exp. Immunol. 28: 1-18, 1977.*
Novotny et al. Develop. Biol. Standard. 73: 243-249, 1991.*
The New Riverside University Dictionary, The Riverside Publishing Company, p. 1056, 1984.*
Weiss et al. Infect. Immun. 57: 2674-2682, 1989.*
De Magistris et al., J. Exp Med 168:1351-1392 1988.*
Novotny et al The Journal of Infectious Dis 164:114-22; 1991.*
Landant et al, "*Bordetella pertussis* adenylate cyclase. Purification, characterization, and radioimmunoassay", J. Biol. Chem. 261(34):16264-162649 (1986).
Guide to Protein Purification (2nd Apr. 1990) Methods in Enzymology, vol. 182, edited by Deutscher.
Preliminary Programme of meeting held on 1st Dec. 1989 at the National Institute for Biological Standards and Control, Potters Bar, UK.
Protein Purification Methods, A Practical Approach, edited by Harris and Angal, Oxford University Press (1989).
Aricò et al., "Adhesion of *Bordetella pertussis* to Eukaryotic Cells Requires a Time-dependent Export and Maturation of Filamentous Hemagglutinin," Proc. Natl. Acad. Sci. USA, 90:9204-9208 (Oct. 1993).
Black et al., "ADP-Ribosyltransferase Activity of *pertussis* Toxin and Immunomodulation by *Bordetella pertussis,*" Science, 240:656-657 (1988).
Brennan et al., "Structural and Functional Properties of a 69-Kilodalton Outer Membrane Protein of *Bordetella pertussis,*" Tokai J. Exp. Clin. Med., 13[suppl]:211-215 (1988).
Brennan et al., "Structural and Functional Properties of a 69-Kilodalton Outer Membrane Protein of *Bordetella pertussis,*" 5th International Symposium on pertussis, Sep. 22-23, 1988, Copenhagen.
Charles et al., "Molecular Cloning and Analysis of p69, a *vir*-controlled Protein from *Bordetella pertussis,*" Tokai J. Exp. Clin. Med., 13[suppl]:237-234 (1988).
Charles et al., "Molecular Cloning and Analysis of p69, a *vir*-controlled Protein from *Bordetella pertussis,*" Abstract/Proceedings of the 5th International Symposium on pertussis, Sep. 22-23, 1988, Copenhagen.
Cherry et al., "A Search for Serologic Correlates of Immunity to *Bordetella pertussis* Cough Illnesses," Vaccine, 16(20):1901-1906 (Dec. 1998).
Cowell et al., "The Filamentous Hemagglutinin and Fimbriae of *Bordetella pertussis*: Properties and Roles in Attachment," in *Microbiology,* ed. L. Leive, pp. 55-58 (1986). Washington, D.C.: Am. Soc. Microbiol.
Edwards et al., "Acellular *pertussis* Vaccines for Infants," The New England Journal of Medicine, 334(6):391-392 (Feb. 8, 1996).
Goldman, "*Bordetella pertussis* Tracheal Cytotoxin: Damage to the Respiratory Epithelium," in *Mircobiology,* ed. L. Leive, pp. 65-69 (1986). Washington, D.C.: Am. Soc. Microbiol.
Gould-Kosta et al., "Purification of a 69,000 Da Outer Membrane Protein form *B. pertussis,*" Abstract /1989 Annual Meeting of the American Society of Microbiology, p. 51, B-126.
Gould-Kosta et al., "Purification and Analysis of the Antigenicity of a 69 000 Da Protein from *Bordetella pertussis,*" FEMS Microbiology Letters, 67:285-290 (1990).
Hewlett et al., "Soluble Adenylate Cyclase form the Culture Medium of *Bordetella pertussis*: Purification and Characterization," J. Bacteriol. 127:890-898 (1976).
Hewlett et al., "Adenyl Cyclase in *Bordetella pertussis* Vaccines," J. Inf. Disease, 136 Supplement, 216-219 (1977).
Hewlett et al., "Virulence Factors of *Bordetella pertussis,*" in *Microbiology,* ed. L. Leive, pp. 53-54 (1986). Washington, D.C.: Am. Soc. Microbiol.
Hewlett et al., "*pertussis* Toxin: Mechanism of Action, Biological Effects, and Roles in Clinical *pertussis,*" in *Microbiology,* ed. L. Leive, pp. 75-78 (1986). Washington D.C.: Am. Soc. Microbiol.
Hewlett et al., in *Microbiology,* ed. L. Leive, p. 79 (1986). Washington, D.C.: Am. Soc. Microbiol.
Hewlett, Prof., Declaration dated Apr. 11, 1991, filed in U.S. Appl. No. 07/521,741.
Montaraz et al., "Identification of a 68-Kilodalton Protective Protein Antigen from *Bordetella bronchiseptica,*" Infect. Immun., 47(3):744-751 (Mar. 1985).
Novotny et al., "A Novel Bivalent Acellular *pertussis* Vaccine Based on the 69 kDa Protein and FHA," Develop. Biol. Standard, 73:243-249 (S. Karger, Basel, 1991).
Novotny et al., "Recent Developments in *pertussis* Research," J. Med. Microbiol., 35:174-190 (1991).
Novotny et al., Abstract of Presentation entitled, "*Bordetella* Specific Protective Antigen", International Workshop on *Bordetella pertussis,* Hamilton, Montana, Aug. 18-20, 1988.
Podda et al., "Phase I Clinical Trial of an Acellular *pertussis* Vaccine Composed of Genetically Detoxified *pertussis* Toxin Combined with FHA and 69 kDa," Vaccine, 9:741-745 (Oct. 1991).
Redhead et al., "Serum Antibody Responses on the Outer Membrane Proteins of *Bordetella pertussis,*" Infect. Immun., 44:724-729 (1984).
Robinson et al., "*pertussis* Vaccine: Present Status and Future Prospects," Vaccine, 3:11-22 (Mar. 1985).
Shahin et al., "Characterization of the Protective Capacity and Immunogenicity of the 69-kD Outer Membrane Protein of *Bordetella pertussis,*" J. Exp. Med., 171:63-73 (Jan. 1990).
Tuomanen, "Adherence of *Bordetella pertussis* to Human Cilia: Implications for Disease Prevention and Therapy," in *Microbiology,* ed. L. Leive, pp. 59-64 (1986). Washington, D.C.: Am. Soc. Microbiol.
Wardlaw et al., "*pertussis* vaccine," Medical Microbiology vol. 2, "Immunization Against Bacterial Disease," Academic Press, (1983).
Weiss et al., "*Bordetella pertussis* Adenylate Cyclase Toxin: Structure and Possible Function in Whooping Cough and the *pertussis* Vaccine," in *Microbiology,* ed. L. Levie, pp. 70-78 (1986). Washington, D.C.: Am. Soc. Microbiol.
Weiss et al., "Tn5-Induced Mutations Affecting Virulence Factors of *Bordetella pertussis,*" Infection and Immunity, 42(1):33-41 (Oct. 1983).
Infanrix™, "Infanrix™ Diphtheria and Tetanus Toxoids and Acellular *pertussis* Vaccine Adsorbed," Product brochure dated Jan. 1997.

ACEL-IMUNE®, Physicians Desk Reference, 52nd Edition, 1998.
Program of International Workshop on *Bordetella pertussis* of Aug. 18-20, 1988, Rocky Mountain Laboratories, Hamilton, Montana.
Declaration of Dr. Rappuoli, dated Jan. 17, 1997, with exhibits RR-1 and RR-2, filed by Chiron in EPO Opposition to European Patent No. 0 471 726.
Second Declaration of Dr. Rappuoli, dated Jun. 26, 1997, filed by Chiron in EPO Opposition to European Patent No. 0 471 726.
Supplemental Arguments for Opposition by Chiron Corporation to European Patent No. 0 471 726, dated Oct. 7, 1997, in EPO Opposition.
Pleadings in Reply in Interim Injunction Proceedings, dated 10th Apr. 1997, in District Court of the Hague.
Pleadings on Behalf of Medeva B. V., dated 15th Jul. 1997, in District Court of the Hague.
*Pertussis* Toxin and Immuned Modulation by *Bordetella pertussis*.
Loosmore et al., "The New Generation of Recombinant *pertussis* Vaccines," in Kurstak, E., ed., *Modern Vaccinology*, Plenum Medical, New York, 1994, pp. 319-340.
Guiso et al., "Intranasal murine model of *Bordetella pertussis* infection: I. Prediction of protection in human infants by acellular vaccines," *Vaccine*, 17:2366-2376 (1999).
Boursaux-Eude et al., "Intranasal murine model of *Bordetella pertussis* infection: II. Sequence variation and protection induced by a tricomponent cellular vaccine," *Vaccine*, 17:2651-2660 (1999).
Oct. 3, 2000 letter to the EPO from Medeva BV in Opposition to EP 471 726 (4 pages).
Sep. 26, 2000 Declaration of Philippe Denoel in Oposition to EP 471 726 (25 pages).
Sep. 22, 2000 Declaration of Georges Carletti in Opposition to EP 471 726 (10 pages).
Sep. 27, 2000 Declaration of Charalambos Panayiotis Kyriacou in Opposition to EP 471 726 (22 pages).
Oct. 11, 2000 Letter to the EPO from Connaught Laboratories Limited in Opposition to EP 471 726 (15 pages).
Oct. 19, 2000 Letter to the EPO from Connaught Laboratories Limited in Opposition to EP 471 726 (25 pages).
Oct. 27, 2000 Letter to the EPO from Medeva BV in Opposition to EP 471 726 (6 pages).
Oct. 2000 Declaration of Peter Knight in Opposition to EP 471 726 (20 pages).
Oct. 27, 2000 Letter to the EPO from Chiron Corporation in Opposition to EP 471 726 (9 pages).
Oct. 27, 2000 Second Affidavit of Prof. dr. J.C. van Houwelingen in Opposition to EP 471 726 (4 pages).
Affidavit of Professor Jack Murphy in Oppositon to EP 471 726 (2 pages).
Oct. 27, 2000 Submissions of Connaught Laboratories Limited in Preparation for Oral Proceedings in Opposition to EP 471 726 (30 pages, including cover letter).
Oct. 27, 2000 Declaration of John Sparkes in Opposition to EP 471 726 (16 pages).
Oct. 27, 2000 Declaration of Kingston Henry Gordon Mills in Opposition to EP 471 726 (29 pages).
Hewlett, "Preparation and Composition of Acellular *pertussis* Vaccines. Consideration of Potential Effects on Vaccine Efficacy," *pertussis* Vaccine Trials, *Dev. Biol. Stand.*, 89:143-151 (1997).
Edwards et al., "Comparison of Serological Results in the NIAID Multicenter Acellular *pertussis* Trial with Recent Efficacy Trials," *pertussis* Vaccine Trials, *Dev. Biol. Stand.*, 89:265-273 (1997).
Wassilak et al., "Rapporteurs' Summary, " *pertussis* Vaccine Trials, *Dev. Biol. Stand.*, 89:187-193 (1997).
Sep. 13, 2000 Letter from Wakabayashi Patent Agency to Aventis Pasteur Limited regarding the Japanese patent application corresponding to EP 471 726 (11 pages).
Nov. 14, 2000 Letter to the EPO from Connaught Laboratories Limited in Opposition to EP 471 726 (6 pages).
Sep. 19, 2000 Declaration of Peter A. Knight filed in *Medeva B. V. v. Chiron S.p.A.*, Court of Milan, Italy, G.R. 10266/98 (2 pages).
Third Technical Memorandum on the Plaintiff's Behalf filed in *Medeva B. V. v. Chiron S.p.A.*, Court of Milan, Italy, G.R. 10266/98 (11 pages).

Third Technical Brief on Behalf of the Defendant filed in *Medeva B. V. v. Chiron S.p.A.*, Court of Milan, Italy, G.R. 10266/98 (10 pages).
Decision of the Opposition Division Revoking EP 471 726 (Apr. 27, 2001).
Oppositions to EP No. 471 726- Properietor's statement of Grounds of Appeal Aug. 10, 2001, 22 Pages.
Third Declaration of Peter Knight Aug. 4, 2001 including three exhibits (I, Ib, Ic) 22 pages.
Weiss et al., "*pertussis* Toxin and Extracytoplasmic Adenylate Cyclase as Virulence Factor of *Bordetella pertussis*," *The Journal of Infectious Diseases*, 150(2):219-222 (Aug. 1984).
Roop II et al., "Virulence Factors of *Bordetella bronchiseptica* Associated with the Production of Infectious Atrophic Rhinitis and Pneumonia in Experimentally Infected Neonatal Swine," *Infection and Immunity*, 55(1):217-222 (Jan. 1987).
Hewlett et al., "Adenylate Cyclase Toxin of *Bordetella pertussis*," in Wardlaw et al., eds., *Pathogenesis and Immunity in pertussis*, John Wiley & Sons Ltd., Surrey, England, 1988, pp. 193-209.
Hewlett et al., "Adenylate Cyclase Toxin from *Bordetella pertussis*," *The Journal of Biological Chemistry*, 264(32):19379-19384 (1989).
Hewlett, "*Bordetella* Species," in *Mandell, Douglas, and Bennett's Principles and Practice of Infectious Diseases Fifth Edition*, vol. 2, Churchill Livingstone, Kent United Kingdom, 2000, Chapter 219, pp. 2414-2422.
Hewlett et al., "New and Improved Vaccines Against *pertussis*," *New Generation Vaccines*, Marcel Dekker, New York, 1997, pp. 387-416.
Masure et al., "Characterization of the Bacterial Cell Associated Calmodulin-Sensitive Adenylate Cyclase from *Bordetella pertussis*," *Biochemistry*, 28:438-442 (1989).
Masure et al., "Secretion of the *Bordetella pertussis* Adenylate Cyclase from *Escherichia coli* Containing the Hemolysin Operon," *Biochemistry*, 29:140-145 (1990).
Rogel et al., "Adenylate Cyclase Toxin from *Bordetella pertussis*," *The Journal of Biological Chemistry*, 266(5):3154-3161 (Feb. 15, 1991).
Masure et al., "Purification and Assay of Cell-Invasive Form of Calmodulin-Sensitive Adenylyl Cyclase from *Bordetella pertussis*," *Methods in Enzymology*, 195:137-152 (1991).
Gotto et al., "Biochemical and Immunological Properties of Two Forms of Pertactin, the 69,000-Molecular-Weight Outer Membrane Protein of *Bordetella pertussis*," *Infection and Immunity*, 61(5):2221-2215 (May 1993).
"Placebo-Controlled Trial of Two Acellular *pertussis* Vaccines in Sweden—Protective Efficacy and Adverse Events," *The Lancet*, pp. 955-960 (Apr. 30, 1988).
Tuomanen et al., "Characterization of Two Adhesins of *Bordetella pertussis* for Human Ciliated Respiratory-Epithelial Cells," *The Journal of Infectious Diseases*, 152(1):118-125 (Jul. 1985).
Manclark et al., "Prospects for a New Acellular *pertussis* Vaccine," *Ann. Inst. Pasteur Microbiol.*, 136 B, 323-329 (1985).
Dzhaparidze et al., "O-Antigen of Vibrio Cholerae, Serovar Ogawa, for the Preparation of Oral Cholera Bivalent Vaccine," *Zhurnal. Mikrobiol. Epidemiol. Immunobiol.*, 11:75-81 (1981).
Bloom, "New Approaches to Vaccine Development," *Reviews of Infectious Diseases*, 11:S460-S466 (Mar.-Apr. 1989).
Miller et al., "Coordinate Regulation and Sensory Transduction in the Control of Bacterial Virulence," *Science*, 243:916-922 (Feb. 17, 1989).
Parker et al., in Atassi et al., eds., Immunology of Proteins & Peptides—III, Viral and Bacterial Antigens, Plenum Press, New York, 1986, pp. 117-127.
Goldhammer et al., Anal. Biochem., 124:45-52 (1982).
Robinson et al., Infect Immun., 39:590-598 (1983).
Parton et al., J. Med. Microbiol., 8:47-57 (1975).
Jun. 18, 2002 Official Action in Japanese Patent Application No. 2002-002530.
Aug. 20, 2002 Official Action in European Patent Application No. 96112324.7.
Product Insert for DAPTACEL® Vaccine, Aventis Pasteur, Aug. 2002.
Oct. 15, 2002 Observations by a Third Party in European Patent Application No. 96112324.7.

Dec. 24, 2002 Response in Japanese Patent Application No. 2002-002530.

Dec. 3, 2002 Complaint in *Celltech Pharmaceuticals Limited* v. *GlaxoSmithKline Corp.*, (M.D. Pa. 2002).

Product Insert for INFANRIX® Vaccine, SmithKline Beecham, Dec. 2002.

Jan. 21, 2003, Notice of Voluntary Dismissal in *Celltech Pharmaceuticals Limited* v. *GlaxoSmithKline Corp.*, (M.D. Pa. 2002).

Feb. 12, 2003 Second Declaration of Peter Knight in European Patent Application No. 96112324.7.

Feb. 13, 2003 Letter to the European Patent Office from J.A. Kemp & Co. in European Patent Application No. 96112324.7.

Feb. 13, 2003 Applicant's Observations in Response to Examination Report and Third Party Observations in European Patent Application No. 96112324.7.

Feb. 2004 Written Submissions Prior to Oral Proceedings submitted by Chiron Corporation in Opposition to European Patent No. 0471726 (2 Pages).

Feb. 19, 2004 Letter to the European Patent Office forwarding Proprietor's Submissions in Preparation for Oral Proceedings and Response to Opponent 1's Observations of Jun. 5, 2002 and claims for a new main request and an auxiliary request (37 Pages).

Feb. 5, 2004 Fourth Declaration of Peter Knight in Opposition to European Patent No. 0471726 (3 Pages).

Feb. 16, 2004 Declaration of Dennis Stainer in Opposition to European Patent No. 0471726 (1 Page).

Feb. 10, 1998 Appellant 0111-Final Submission in Opposition to European Patent No. 0162639 (34 Pages).

Nov. 3, 1995 Grounds of Appeal by Connaught Laboratories Ltd. in Opposition to European Patent No. 0471726 (19 Pages).

Definition of "aggregate" from Cambridge Dictionaries Online, 2004 (1 Page).

Definition of "aggregate" from Merriam-Webster Online Dictionary, 2004 (2 Pages).

Feb. 11, 2004 Declaration of Erik Hewlett in Opposition to European Patent No. 0471726 (3 Pages).

Roberts et al., "Construction and Characterization of *Bordetella pertussis* Mutants Lacking the *vir*-regulated P. 69 Outer Membrane Protein," Molecular Microbiology, 5(6):1393-1404 (1991).

Jan. 21, 2004 Summons to Attend Oral Proceedings in European Patent Application No. 96112324.7 (6 Pages).

Sep. 23, 2003 Letter to the European Patent Office responding to a Jul. 10, 2003 Examination Report in European Patent Application No. 96112324.7 and forwarding a dictionary definition and claims for a new main request and an auxiliary request (16 Pages).

Jul. 10, 2003 Official Action in European Patent Application No. 96112324.7.

Jun. 18, 2004; Minutes of the May 25, 2004 Oral Hearing in European Patent Application No. 96112324.7 (31 pages).

Mar. 29, 2004; Minutes of the Mar. 19, 2004 Oral Proceedings in Opposition to European Patent No. 0471726 (3 pages).

Complete text of European Patent Applications No. 96112324.7 indicated to be allowed at an Oral Hearing on May 25, 2004 (18 pages).

Jun. 28, 2004, Notice of Allowance in European Patent Application No. 96112324.7 (22 pages).

J.A. Kemp & Co., Cover Letter to the EPO dated Jul. 19, 2004, Opposition to European Patent No. 0471726 (1 page).

Proprietor's Submissions in Advance of Second Oral Proceedings in Opposition to European Patent No. 0471726 dated Jul. 19, 2004, (15 pages).

Carpmaels & Ransford, Cover Letter to the EPO dated Jul. 19, 2004, Opposition to European Patent No. 0471726 (1 page).

Chiron Corporation, Written Submissions dated Jul. 2004, Oppositions to European Patent No. 0471726 (12 pages).

English Translation of Sep. 22, 2004 Written Demand for Trial Regarding Japanese Patent No. 3,295,478, including exhibits and reference materials.

English Translation of Sep. 22, 2004 Written Demand for Trial Regarding Japanese Patent No. 3,140,776, including exhibits and reference materials.

Written Statement by the Defendant in Japanese Invalidation No. 2004-80157, regarding Japanese Patent No. 3281369 (13 pages in Japanese and 15 pages of English translation), Jul. 14, 2005.

Written Statement by the Demandant in Japanese Invalidation No. 2004-80157, regarding Japanese Patent No. 3281369 (20 pages in Japanese, 13 pages of exhibits, and 38 pages of English translation), Jul. 14, 2005.

Document A submitted by Demandant at Jun. 14, 2005 Oral Hearing in Japanese Invalidation No. 2004-80157, regarding Japanese Patent No. 3281369 (1 page, with added notations in English).

Document B submitted by Demandant at Jun. 14, 2005 Oral Hearing in Japanese Invalidation No. 2004-80157, regarding Japanese Patent No. 3281369 (2 pages in Japanese and 2 pages of English translation).

Communication of a Notice of Opposition to European Patent No. 0 747 058 (cover page (1 page), Notice of Opposition (21 pages), and 17 supporting documents), Jul. 6, 2005.

Guiso et al.: "Intranasal murine model of *Bordetella pertussis* infection. I. Prediction of protection in human infants by acellular vaccine"; Vaccine 17 (1999) 2366-2376.

Boursaux-Eude et al.: "Intranasal murine model of *Bordetella pertussis* infection: II. Sequence variation and protection introduced by a tricomponent acellular vaccine"; Vaccine 17 (1999) 2651-2660.

*Evans Medical Ltd, Medeva PLC and SmithKline Beecham et al* v. *American Cyanamid et al*, 98-1446,—1459 (U.S. Court of Appeals for the Federal Circuit, Decided Aug. 9, 1999).

Bernardini et al., Journ. Bact. 172:6274-6281, 1990.

Liljestrom et al., Mol. Gen. Genet., 188:184-189, 1982.

Tagliabue et al., Tokai J. Exp. Med., 13 Suppl.:253-257, 1988.

Chatfield et al., Vaccine, 7:495-498, 1989.

Corbel et al., Dev. Biol. Stand., 89:343-347, 1997.

Corbel et al., J. Med. Microbiol., 25:174-175, 1991.

Nicosia et al., Proc. Natl. Acad. Sci., 83:4631-4635, 1986.

Relman et al., Proc. Natl. Acad. Sci., 86:2637-2641, 1989.

Brown et al., Infection and Immunity, 55:154-161, 1987.

Robinson et al., Infection and Immunity, 40:523-528, 1983.

Munoz et al., Microbiol. Immunol., 33(4):341-355, 1989.

Roberts, et al., Molecular Microbiology, 5:1393-1404, 1991.

DeMagistris et al., J. Exp. Med., 168:1351-1362, 1988.

Pillemer, L., Proceedings of the Society for Experimental Biology and Medicine, 75:704-705, 1950.

J. Infectious Diseases 1991: 164:114-22 Novotny et al "Biologic and Protective Properties of the 69-kDA . . . ".

Ann. Rev. Microbiol. 1986, 40:661-86 Weiss et al "Virulence Factors of *Bordetella pertussis*".

J. Infectious Diseases vol. 159, No. 1 Feb. 1989 pp. 211-218 Thomas et al "Human Serum Antibody to *Bordetella* . . . ".

Infection and Immunity vol. 56, No. 12, Dec. 1988, pp. 3189-3195 Brennan et al "Identification of a 69-kilodalton . . . ".

J. Ex. Med. vol. 168 Oct. 1988 pp. 1351-1362 De Magistris et al "Dissecting Human T Cell Responses . . . ".

JAMA, Jul. 2, 1982 vol. 248, No. 1 "Newer *pertussis* vaccines on horizon".

Reviews of Infectious Diseases vol. 1, No. 3, May-Jun. 1979 Pittman "*pertussis* Toxin: The Cause of the Harmful Effects and Prolonged Immunity of Whooping Cough. A Hypothesis".

Sep. 26, 2005 letter from J.S. Kemp & Co. to the EPO in Opposition to EP 0 471 726 (12 pages).

Sep. 26, 2005 letter from Carpmaels & Ransford to the EPO in Opposition to EP 0 471 726 (5 pages).

Nov. 2, 2005 Minutes of Oral Proceedings in Opposition to EP 0 471 726 (9 pages).

"Decision of Appeal in corresponding JP3281369," Dec. 13, 2006.

Arai et al., "Fimbrial Hemagglutinin in Stationary and Shake Cultures of *Bordetella pertussis*," Infect. Immun., 25(2):764-767 (1979).

Ashworth et al., "Antigenic Relationship Between Serotype-Specific Agglutinogen and Fimbriae of *Bordetella pertussis*," Infect. Immun., 37(3):1278-1281 (1982).

Cowell et al., "Separation, Purification, and Properties of the Filamentous Hemagglutinin and the Leukocytosis Promoting Factor-Hemagglutinin From *Bordetella pertussis*," Seminars in Infectious Disease, vol. IV: Bacterial Vaccines, Thieme-Stratton Inc., New York, 1982, pp. 371-379.

Sato et al., "Separation and Purification of the Hemagglutinins from *Bordetella pertussis*," Infect. Immun., 41(1):313-320 (1983).

Weiss et al., "Transposon Insertion and Subsequent Donor Formation Promoted by Tn501 in *Bordetella pertussis*," Journal of Bacteriology, Jan. 1993, p. 304-309, vol. 153, No. 1.

Brennan et al., "Identification of a 69-Kilodalton Nonfimbrial Protein As an Agglutinogen of *Bordetella pertussis*," Infection and Immunity, Dec. 1988, p. 3189-3195, vol. 56, No. 12.

Munoz et al., "Role of Pertussigen (*pertussis* Toxin) on the Mouse Protective Activity of Vaccines Made from *Bordetella* Species," Microbiol. Immunol. vol. 33 (4), pp. 341-355, 1989.

Decision in Case No. T 0780/95—3.3.4, Board of Appeals of the European Patent Office, Mar. 11, 1998.

Lewis et al., "A Double-Blind Study Comparing an Acellular *pertussis*-Component DTP Vaccine With a Whole-Cell *pertussis*-Component DTP Vaccine in 18-Month-Old Children," AJDC, 140:872-876 (Sep. 1986).

Pichinchero et al., "Acellular *pertussis* Vaccine: Immunogenicity and Safety on an Acellular *pertussis* vs. a Whole Cell *pertussis* Vaccine Combined with Diphtheria and Tetanus Toxoids as a Booster in 18- to 24-Month Old Children," The Pediatr. Infect. Dis. J., 6(4):352-363 (1987).

Edwards et al., "Diphtheria, Tetanus, and *pertussis* Vaccine," AJDC, 140:867-871 (Sep. 1986).

Reed et al., "A Simple Method of Estimating Fifty Per Cent Endpoints," The American Journal of Hygiene, 27(3):493-497 (May 1938).

Partial European Search Report in EP 040 18329, search completed Apr. 23, 2008.

Diagram of the *B. pertussis* cell: a schematic representation.

Redhead, Keith et al., "A Collaborative Assay of the Proposed Third British Reference Preparation for *pertussis* Vaccine and of the Relative Potencies of the Second International Standard and the Second British Reference Preparation *pertussis* Vaccine," Biologicals, 1991, pp. 107-111, vol. 19, The International Association of Biological Standardization.

Information about British reference vaccine 88/522, National Institute for Biological Standards and Control, pp. 1-7, UK.

Proscribing information for the vaccine INFANTRIX of SmithKline Beecham, pp. 1-23.

Burns et al., "US Patent App: Process for the Purification of a 69,000 Da Outer Membrane Protein of *Bordetella pertussis*," US Department of Commerce National Technical Information Service (NTIS), Feb. 10, 1989.

Charles, Ian G. et al., "Molecular Cloning and Analysis of P. 69, a *vir*-controlled Protein from *Bordetella pertussis*," Tokai J. Exp. Clin. Med., 1988, pp. 227-234, vol. 13 suppl.
Announcement entitled, "Chiron Biocine Genetically Engineered Acellular *pertussis* Vaccine Proves Superior to Currently Licensed Vaccine," Business Wire, Jul. 13, 1995, Gale Group, Farmington Hills, Michigan.
Pickering, Larry K. et al., "Recent Advances in *pertussis* Immunization," Pediatric Infectious Diseases, Mar. 1997, vol. II No. 3, National Foundation for Infectious Diseases.
Munoz, John J. et al., "Role of Pertussigen (*pertussis* Toxin) on the Mouse Protective Activity of Vaccines Made from *Bordetella* species," Microbiol. Immunol., 1989, pp. 341-355, vol. 33 No. 4.
Physican's Desk Reference (1994), pp. 1149-1151.
Bundle of *PubMed* abstracts that use the word "evitable."
Results of an epoline search for European patents and applications naming Dr. Rappouli as an inventor, Apr. 23, 2004.
Airaksinen et al., *Biotechnological Letters*, 13(5):305-310 (1991).
Brennan et al., Abstract B-2, Annual Meeting of American Society of Microbiology, p. 30, (1988).
Brownlie et al., *Microbial Pathogenesis*, 1988, 4:335-344.
Burns et al., *Chemical Abstracts*, 112, p. 395, Abstract No. 1048386b ($19^{th}$ Mar. 1990).
Charles et al., *Eur. J. Immunol.*, 21:1147-1153 (1991).
Charles et al., *Research in Microbiology*, 144(9):681-690 (1993).
Glaser et al., *EMBO J.*, 12:3997-4004 (1988).
Gould-Kostka et al., Abstract B-126, Annual Meeting of the American Society of Microbiology, p. 51, (1989).
Gould-Kostka et al., *FEMS Microbiol. Letters*, 67:285-290 (Mar. 1990).
Ladant et al., *The Journal of Biological Chemistry*, 261:16264-16269 (1986).
Makoff et al., *Bio/Technology*, 8:1030-1033 (Nov. 1990).
Makoff et al., *Nucleic Acids Research*, 19(9):2417-2421 (1991).
Mooi et al., *Infection and Immunity*, 66(2):670-675 (1998).
Nara et al., *The Journal of Biological Chemistry*, 264:19308-19312 (1989).
Oxer et al., *Nucleic Acids Research*, 19(11):2889-2992 (1991).
Pagliaccia et al., *Arch Microbiol.*, 168:437-440 (1997).
Palczewski et al., *The Journal of Biological Chemistry*, 263:14067-14073 (1988).
Pazirandeh et al., *The Journal of Biological Chemistry*, 264:18195-18201 (1989).
Pizza et al., *Science*, 246:497-500.
Scopes, *Analytical Biochemistry*, 165:235-246 (1987).
Strugnell et al., *Infection and Immunity*, 60(10), 3994-4002 (1992).
Swarup et al., *Biochem. J.*, 251:569-576 (1998).
Tuomanen et al., *Develop. Biol. Standard*, 1985, 61;197-204.
Vose, abstract of Lecture of $1^{st}$ Dec. 1989, J. Med. Microbiol., vol. 35, p. 187 (1991).
Weiss et al., *Ann. Rev. Microbiol.*, 40:661-686 (1986).
Weiss et al., *Dev. Biol. Stand.*, 61:11-19 (1985).
Weiss et al., *Infect. and Immun.*, 57(12):3757-3764 (1989).
Bulletin 1107 from Bio-Rad, Oct. 1986.
Catalog of Sigma Chemical, pp. 1750-1763 (1996).
Amino acid sequence of Bifunctional Hemolysin-Adenylate Cyclase protein (P15318) from *B. pertussis* taken from the Swiss Institute of Bioinformatics database (1 page), Jul. 2001.
Figure 3, from Montaraz et al. (1985). (Lowry Report Tab G1) Analysis of fractions obtained by BB05-based affinity chromatography (1 page), Apr. 2001.
Figure 5, from Brennan et al. (1988) (Hewlett Statement Tab P) Identification of antigenically similar proteins in *B. bronchiseptica* and *parapertussis* (1 page), Jul. 2001.
Figure 1 from UK patent application 8412207 Example 2 (Lowry Report Tab D) Separation of *B. pertussis* crude outer membrane protein (from acid glycine hydrolysis) on a DEAE-Trisacryl column and Overlay: Figure 1(a) from Novotny et al. (1985) (Lowry Report Tab G3) Separation of acid glycine hydrolysate of *B. bronchiseptica* LBF on a DEAE-Trisacryl column (2 pages), Apr. 2001.
Greenlee et al., "Calcium-Independent Stimulation of *Bordetella pertussis* Adenylate Cyclase by Calmodulin," *Biochemistry*, 21:2759-2764 (1982).
Finn et al., "Tracheal Colonization Factor: a *Bordetella pertussis* Secreted Virulence Determinant," *Molecular Microbiology*, 16(4):625-634 (1995).
Laue et al., "Computer-Aided Interpretation of Analytical Sedimentation Data for Proteins," in Harding et al., eds., *Analytical Ultracentrifugation in Biochemistry and Polymer Science*, Royal Society of Chemistry, London, 1992, pp. 90-125.
Hewlett et al., "Extracytoplasmic Adenylate Cyclase of *Bordetella pertussis,*" *Proc. Nat. Acad. Sci. USA*, 73(6):1926-1930 (Jun. 1976).
Hewlett et al., "Regulation of *Bordetella pertussis* Extracytoplasmic Adenylate Cyclase," *Advances in Cyclic Nucleotide Research,* vol. 9, Raven Press, New York, 1978, pp. 621-628.
Weiss et al., "*Bordetella pertussis* Adenylate Cyclase Toxin: Structure and Possible Function in Whooping Cough and the *pertussis* Vaccine," in L. Leive, ed., *Microbiology,* American Society for Microbiology, Washington, D.C., 1986, pp. 70-74.
Judgment Pursuant to 37 CFR § 1,862 for Interference Nos. 104,589 and 104,590, Feb. 2002.
Chiron's Response to Patentee's Appeal Regarding Oppositions to European Patent No. 0471726 (25 pages), Jun. 2002.
Blom et al., *APMIS,* 102:681-689 (1994).
Englund et al., *JID*, 166:1436-1441 (1992).
Mooi et al., *FEMS Microbiology Letters*, 66:327-332 (1990).
Pasteur Mérieux, "The Facts about Acellular *pertussis* Vaccines" (5 pages), Jan. 2003-Aug. 2008.
Apr. 23, 2004 Letter to the EPO regarding response to Summons to Oral Proceedings in Opposition to European Patent No. 0471726 (2 pages).

Apr. 23, 2004 Applicant's Observations in Preparation for Oral Proceedings before the Examining Division and claims in Opposition to European Patent No. 0471726 (21 pages).

Mar. 29, 2004 Minutes of the Oral Proceedings in Opposition to European Patent No. 0471726 (3 pages).

Program of International Workshop on *Bordetella pertussis* held at Rocky Maountain Laboratories, Montana, Aug. 18-20, 1988 (7 pages).

Diagram illustrating the *Bordetella pertussis* cell (1 page), Apr. 23, 2004.

Aug. 20, 1998 Declaration of Ian G. Charles in Opposition to European Patent No. 0471726 (12 pages).

Explanatory Notes extract from Merriam-Webster Dictionary in Opposition to European Patent No. 0471726 (5 pages) Apr. 23, 2004.

Entry for "goody" in Merriam-Webster Dictionary from Opposition to European Patent No. 0471726 (1 page) Apr. 23, 2004.

Results of an EPOLINE search for patents and patent applications for which Dr. Rappuoli is an inventor from Opposition to European Patent No. 0471726 (4 pages), Apr. 23, 2004.

Brief curriculum vitae of Dr. Mark Roberts from Opposition to European Patent No. 0471726 (4 pages) Apr. 23, 2004.

Mar. 10, 2004 Communication Pursuant to Article 115(2) EPC forwarding Feb. 20, 2004 Observations against European patent application No. 96112324,7 and dictionary definition (13 pages).

Nolan et al., "Primary Course Immunogenicity and Reactogenicity of a New Diphtheria-Tetanus-Whole Cell *pertussis* Vaccine (DTP$_w$)," *J. Paediatric. Child Health*, 33:413-417 (1997) (5 pages).

Fletcher et al., "The Efficacy of Whole Cell *pertussis* Immunisation: Collected Data on a Vaccine Produced in France," *Public Health*, 115:119-129 (2001) (11 pages).

Proprietor's Response to Opposition in Opposition to EP0747058, Jul. 3, 2006.

Diagram of the *B. pertussis* cell: a schematic respresentation, Jul. 2006.

Declaration of Arthur Rowe, European Patent No. 0747058, Patentee Medeva BV, Opponent: Chiron Corporation, Jul. 2006.

Information about British reference vaccine 88/522, National Institute for Biological Standards and Control, pp. 1-7, UK, Jul. 2006.

Submission filed by the Opponent on Feb. 10, 1998 in appeal proceedings on an earlier patent of the present inventor, pp. 1-34.

Declaration of Peter A. Knight relating to experiments in inventor Novotny's notebook, Jul. 2006.

Proscribing information for the vaccine INFANTRIX of SmithKline Beecham, pp. 1-23, Jul. 2006.

Announcement entitled, "Chiron Biocine Genetically Engineered Acellular *pertussis* Vaccine Proves Superior to Currently Licensed Vaccine," Business Wire, Jul. 13, 1995, Gate Group, Farmington Hills, Michigan.

Bundle of *PubMed* abstracts that use the word "evitable," Jul. 2006.

European Patent 0471726 (Medeva BV) Opposed By Chiron Corporation (01) Written Submissions Prior to Oral Proceedings, pp. 1-2 (with Dictionary Attachments from The Concise Oxford Dictionary of Current English Eight Edition and The Collins Concise Dictionary of the English Language 2nd Edition), Jul. 2004.

JAMA, Jul. 2, 1982 vol. 248, No. "Newer *pertussis* vaccines on horizon".

Communication pursuant to Article 94(3) EPC in European Patent Application No. 04018329.5 (6 pages) - Aug. 13, 2008.

Communication - Result of Consultation in European Patent Application No. 04018329.5 (2 pages) - Sep. 5, 2008.

Communication - Response to Communication in European Patent Application No. 04018329.5 (5 pages) - Sep. 10, 2008.

Charles et al, "Molecular Cloning and Characterization of Protective Outer Membrane Protein P.69 from *Bordetella pertussis*", Proc. Natl. Acad. Sci. USA, vol. 86, pp. 3554-3558, May 1989, Biochemistry.

\* cited by examiner

ACELLULAR *PERTUSSIS* VACCINE COMPRISING A COMBINATION OF THE 69 KDA AND THE FILAMENTOUS HAEMAGGLUTININ ANTIGENS OF *BORDETELLA PERTUSSIS*

This application is a continuation of application Ser. No. 08/221,451, filed 1 Apr. 1994, now abandoned, which is a continuation of application Ser. No. 08/137,778, filed Oct. 19, 1993, now abandoned, which is a continuation of application Ser. No. 07/773,649, filed Oct. 17, 1991, now abandoned, which was filed as PCT international application PCT/GB90/00649 on Apr. 26, 1990, and claims foreign priority to application 8910570.4 filed May 8, 1989 in the United Kingdom.

The present invention relates to acellular *Bordetella Pertussis* vaccine compositions, in particular to an acellular *Bordetella Pertussis* vaccine comprising a synergistic combination of the 69 kDa antigen and the filamentous haemagglutinin antigen (FHA) from *B. pertussis*, to methods of manufacture of a vaccine composition containing them and to their use in medicine.

*Bordetella pertussis* causes a serious and debilitating disease in humans, children being particularly susceptible, which is kept under control in the developed countries by large scale immunisation programmes. It has been found that immunisation is a very important factor in the reduction of the disease and that failure to vaccinate can lead to increased incidence of the disease. In practically all areas, immunisation is effected using a whole cell *B. pertussis* vaccine which has been found to be relatively effective in preventing the disease. However, recently, concern over adverse reactions to the vaccines has led to lower vaccine acceptance and debate about its continued use.

Some of the adverse reactions noted include fever, local reactions and persistent screaming. The incidence of fewer and persistent screaming have been estimated to occur in 7% of patients (Wardlaw et al Medical Microbiology Vol.2. Immunisation against Bacterial Disease 1983).

With the currently low occurrence of the disease in developed countries with immunisation programmes, the benefit/risk ratio is poorly defined, and many clinicians believe that the risk of inoculation outweigh the benefits gained by immunisation. As a result, many children are not inoculated and there is now a consequent risk of a pandemic of whooping cough. Indeed in recent years the incidence of whooping cough and resulting infant morbidity has increased as the use of the whole cell vaccine has decreased. Considerable research effort has, therefore, been directed towards the development of improved *pertussis* vaccines and especially acellular vaccines which lack the components associated with the toxic effects of the whole cell vaccines which have caused the concerns, whilst incorporating those components necessary to protect against the disease.

The search for a safer, effective, acellular *B. pertussis* vaccine has been hampered in the past by the paucity of information regarding the identity and mechanisms of action of the pathogenic, toxic and protective moieties of *B. pertussis* contained in the whole cell vaccines. Work has, therefore, been concentrated on isolating and purifying the 20 or more surface antigens of the *B. pertussis* organism and characterising their ability to induce immune reactions (see, for example, J. Am. Med. Soc. 248 (1) 22-23). Examples of antigens that have been suggested for investigation include lymphocytosis promoting factor (pertussis toxin/LPF) filamentous haemagglutinin (FHA), lipopolysaccharide (LPS), agglutinogens, dermonecrotic toxin (DNT), heat labile and heat stable toxins, polymorphonuclear leukocyte inhibitor factor, adenylate cycles and other surface components. Other proposed candidate antigens for investigation include tracheal cytotoxin and various outer membrane proteins.

An early extract vaccine was developed by L. Pillemer (Proc. Soc. Exp. Biol. Med. (1950) 75, 704-705) which was based on disrupted *B. pertussis* cells and found to provide protection, but which was not adopted commercially in view of the toxicity of the preparation.

Examples of more recent *B. pertussis* extract vaccines that have been suggested include those described in UK Patent Specification 2 083 358A (Takeda) involving removal of endotoxin from culture supernatants: French Patent Specification 2 047 886 (Institut Merieux) involving extraction of a microbial suspension with an anionic surfactant; and Japanese Patent Specification 58-222032 (Teljin) which comprises a sub-unit protein vaccine based on pertussis toxin (LPF).

Much of the work carried out on acellular *pertussis* vaccines is concentrated on the possibility of basing such a vaccine on LPF. However, it is believed that some of the adverse effects hitherto observed to be associated with *pertussis* vaccination are related to the toxin. In combination with tetanus or diphtheria toxoid and LPS. It is able to induce experimental encephalopathy in susceptible mice (L.S teinman, et al. Nature (1982) 299, 738-740; Redhead et al, Workshop on *B. pertussis*, Nat. Inst. of Biol. Standards & Controls, Holy Hill, Hampstead, London, 1983). Thus some clinicians believe that LPF may, possibly, be responsible for brain damage should such complications occurred after vaccination.

Nonetheless, studies to date, have generated data which has led to a general belief that LPF is an essential part of any acellular vaccine (Bacterial Vaccines, 1984, Chapter 3, Manclark et al, Editor Germanier).

A new acellular vaccine, currently available in Japan has been tested in controlled clinical trials in Sweden. This vaccine includes the pertussis toxin (LPF) and FHA or LPF alone (Lancet 1 995 1988). However this vaccine has proved not to be as effective as a whole cell vaccine, providing only about 69% protection.

Apart from the poor protective affect three deaths occurred in the toxin based vaccine group which may possibly be associated with the vaccine. Considering all these data, the Swedish Health Authority refused to license this so called "Japanese Vaccine" in Sweden.

This clinical trial, however, is an illustration of the belief that LPF antigen is an essential component of the vaccine since it has been suggested that whooping cough is a toxin-mediated disease and that the protection of mice in the pertussis mouse protection test is solely dependent on the presence of an active LPF in the preparation (Pittman, M. 1984: The Concept of Pertussis as a Toxin-Mediated Disease, Pediatric Infection Disease, 3, 467-486). It is believed that these assumptions are incorrect.

Filamentous haemagglutinin (FHA) is a protein having a molecular weight of between 107-130 kDa and appears as filaments in the electron microscope. It is a haemagglutinin that is inhibited by cholesterol.

Many research groups have suggested that FHA may be an important immunogen and vaccine candidate. (For a review see Bacterial Vaccines 1984, Chapter 3, Manclark et al, Editor Germanier). Our data shows however, that FHA alone only provides minimal protection.

The 69 kDa antigen of pertussis is an outer membrane protein is heat-stable and can be prepared by methods known in the art (see EPO162639). The use of 69 kd on its own is not as efficient as the whole cell vaccine.

The present inventors have found, that a combination of 69 kDa and FHA together is, surprisingly more potent than the aggregate effect of the individual components. The synergistic combination of 69 kDa and FHA is advantageous since LPF is not required, and consequently the chances of adverse effects are reduced. Additionally, a bivalent vaccine containing only 69 kDa and FHA will clearly be easier and cheaper to manufacture than a trivalent vaccine containing LPF as well.

Apart from that, by a proper combination of pertussis antigens the equal effective dose of the suggested combination is up to 15 times lower than, for example, a combination of the 69 kDa protein and LPF.

Thus according to the present invention there is provided a pharmaceutical composition comprising in combination, the 69 kDa antigen of *Bordetella pertussis* with the filamentous haemagglutinin antigen in admixture with a pharmaceutically acceptable excipient. It will be appreciated that in this context, pharmaceutical composition encompasses vaccine composition.

There is also provided a synergistic combination comprising i) the 69 kDa antigen from *B. pertussis* and ii) the filamentous haemagglutinin antigen of *B. pertussis* in an amount effective to induce protection in a mammal to subsequent challenge by a virulent strain of *B. pertussis*.

The ratio of 69 kDa antigen to FHA may vary between broad limits (e.g. 1:10 and 10:1), but is preferably approximately 1:1.

The present invention further provides the 69 kDa and FHA antigens for concomitant use for the prophylactic treatment of mammals susceptible to *B pertussis* infections.

Pharmaceutically acceptable excipients maybe liquid media suitable for use as vehicles to introduce the antigen into the patient. An example of such a carrier is saline solution. The antigenic proteins may be in solution or suspended as a solid in the carrier.

The vaccine formulation may also comprise an adjuvant for stimulating the immune response and thereby enhancing the effect of the vaccine. Convenient adjuvants for use in the present invention include, for example, aluminum hydroxide and aluminum phosphate.

Conveniently the vaccine formulations are presented to contain a final concentration of antigenic protein in the range of from 0.01 to 5 mg/ml, preferably 0.03 to 2 mg.ml, most preferably 0.3 mg/ml. After formulation the vaccine may be incorporated into a sterile container which is then sealed and stored at a low temperature, for example 4° C., or may be freeze-dried.

In order to induce immunity in man to whooping cough one or more doses of the vaccine suitable formulated may be administered. It is recommended that each dose is 0.1 to 2 ml preferably 0.2 to 1 ml, most preferably 0.5 ml of vaccine. The present invention, in a further aspect provides a method for inducing immunity to whooping cough in man, comprising the administration of an effective amount of a vaccine formulation, as hereinbefore defined, to the host.

The present invention also includes the use of 69 kDa and FHA in the preparation of a vaccine for use in the induction of immunity to whooping cough in man. The vaccines according to the present invention may be administered by any conventional method for the administration of vaccines including oral and parenteral. The treatment may consist of a single dose or a plurality of doses over a period of time.

Accordingly there is provided a method of treatment of mammal susceptible to *B pertussis* infections comprising the administration either concurrently or sequentially of 69 kDa antigen of *B pertussis* and FHA.

EXAMPLE 1

Preparation of Filamentous Haemagglutinin (FHA)

Figure 1:
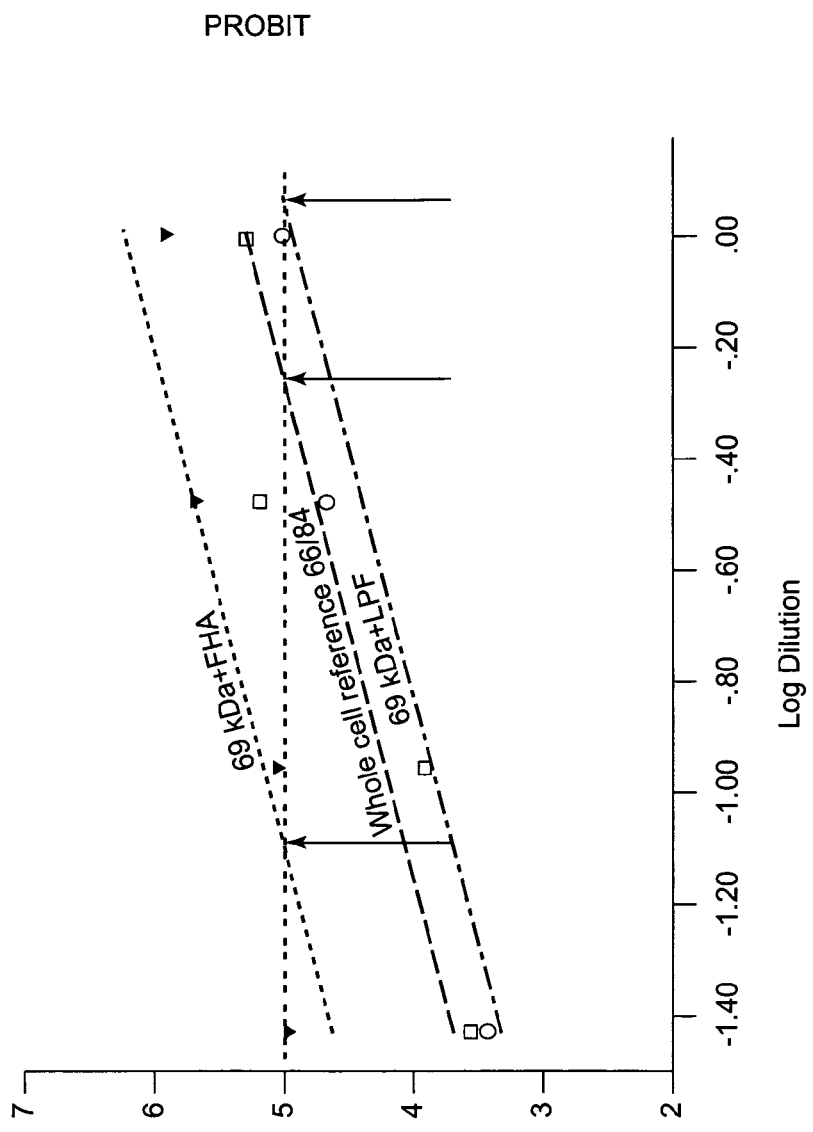
FIG. 1 presents the results obtained in Example 3 and shows the relative potency of 69 kDa protein plus FHA and 69 kDa protein plus LPF in mouse potency assays as related to the whole cell reference 66/84.
Figure 2:
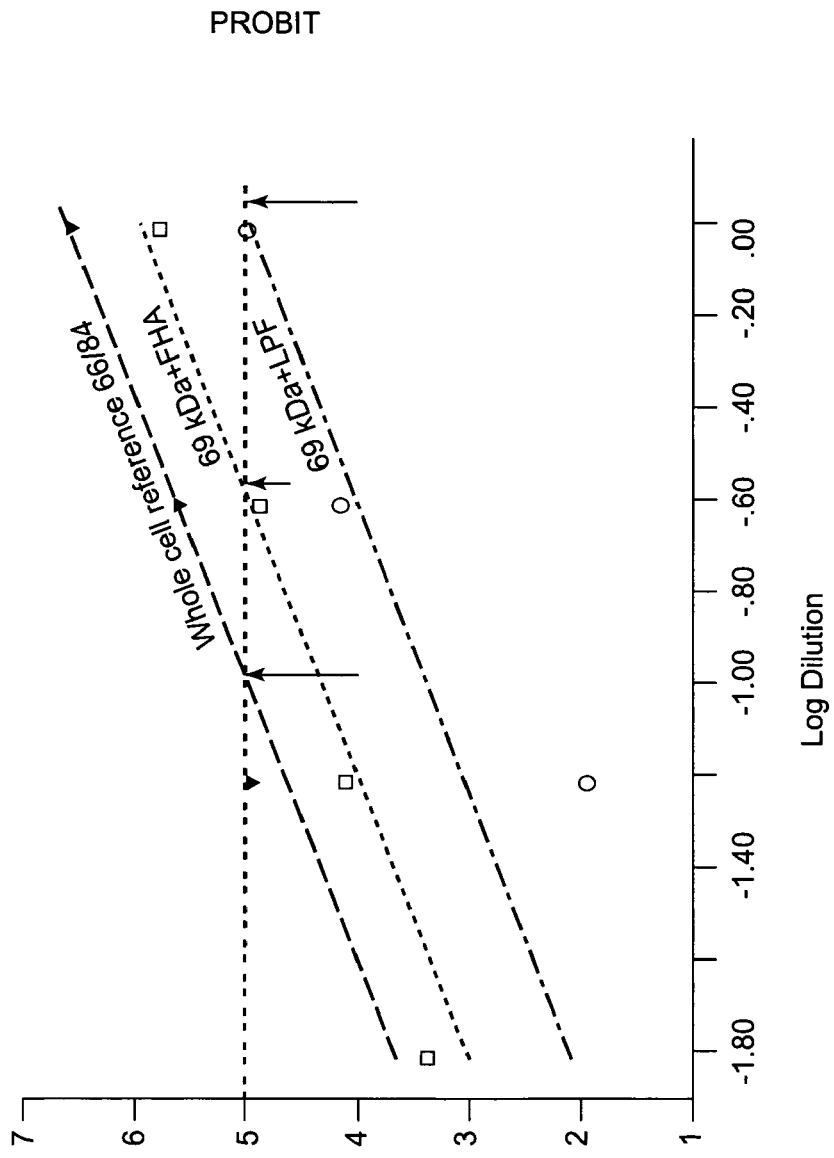
FIG. 2 presents the results obtained in Example 4 and shows the relative potency of 69 kDa protein plus FHA and 69 kDa protein plus LPF in mouse potency assays as related to the whole cell reference 66/84.
Figure 3:
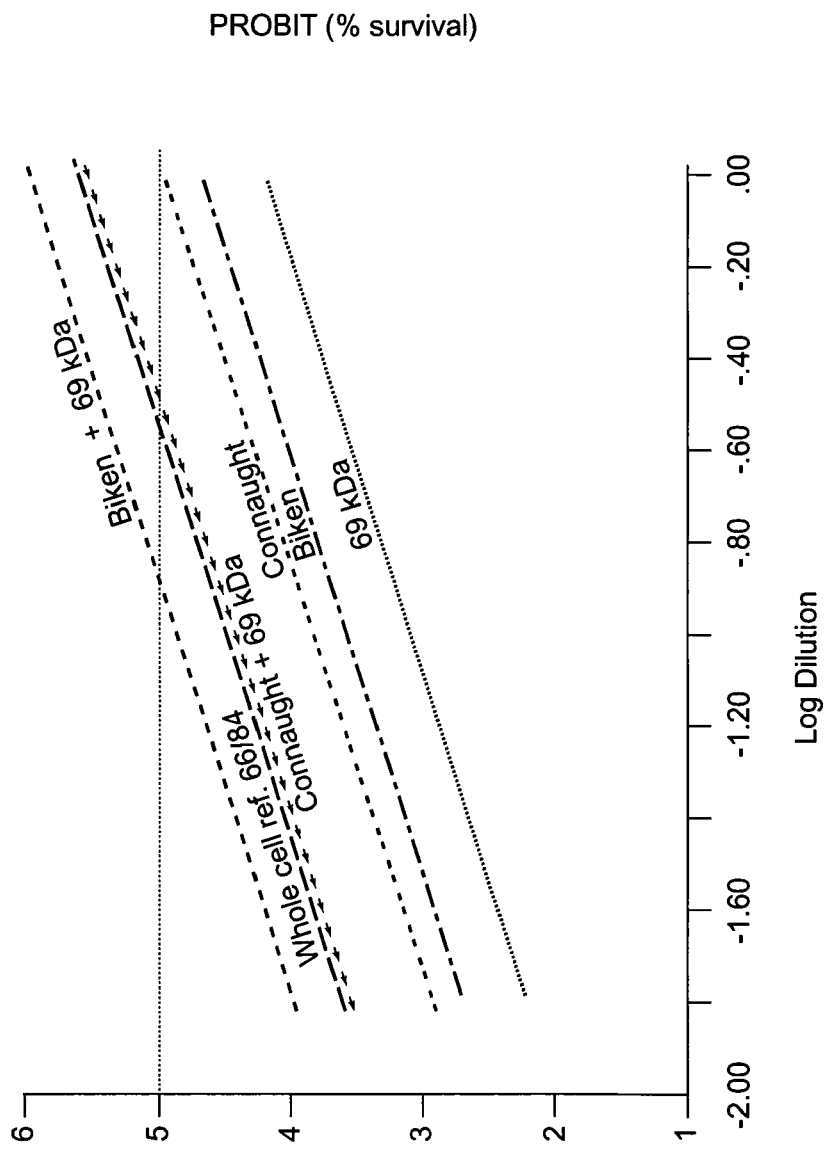
FIG. 3 presents the results obtained in Example 5 and shows the relative potency of subcellular vaccines without and with the addition of 69 kDa protein as related to the whole cell reference 66/84.

FHA can be prepared in methods well known in the art (see Arai H. and Munoz J. J. (1979), *Infect. Immun.* 25:764-767; Ashworth et al (1982) *Infect. Immun.* 37: 1278-1281; Cowell et al, Bacterial Vaccines, p371-379, Seminars in Infectious Diseases Vol. IV (1982); Sato et al (1983) *Infect. Immun.* 41: 313-320). However FHA in the following procedure was prepared in accordance with the following protocol.

FHA Purification

*B. pertussis* Tomaha or BP357 (Tn5 transposon mutant of A A. Weiss et al (1983) which does not secrete the LPF) or W28ΔLPF obtained from R. Rappuloi were grown in Stainer & Scholte medium (0.05 Tris) in 650 ml COSTAR flasks (150 ml in each) for 5 days at 37C (Sato et al 1983 supra). Before centrifugation (30 mins at 6000×g) 50 uM, 1,10-phenanthroline monohydrate as proteolysis inhibitor was added to the cultures. The cell free supernatant adjusted to pH 8.7 (using 5N.NaOH) was applied to a 30×350 mm column of Spheroidal Hydroxyapatite (BHD) at a flow rate of 500 ml/hr. (All operations at room temperature). The column was then washed in the cold room (30 4° C.) until stable baseline was achieved at a flow rate of 50 ml/hr with (a) 10 mM phosphate buffer, pH 8.0, (b) 100 mM phosphate buffer, pH 8.0, and finally (c), the retained material was eluted with 0.5 N.NaCl in 100 mM phosphate buffer, pH 7.0. The peak fractions agglutinating goose red blood cells (10 μl volumes from each fraction suspended in 50 ul of PBS and an equal amount of washed 0.5% goose blood cells were added and incubated for 1-2 hours at 37° C.) were pooled. The Pool was dialyzed overnight against 20-30 volumes of 0.025M Bis-Tris/HCl buffer, pH 7.1, at 4° C. The precipitated FHA was collected on a centrifuge (20 mins at 8000×g). The next step was inspired by Cowell et al (1983) who found that the FHA (as well as LPF) is soluble in 40 mM beta-alanine buffer, pH 3.5. The precipitated FHA was solubilized in the smallest possible volume of β-alanine buffer (3.57 g β-alanine and 0.35 g formic acid per litre), insolubles removed by centrifugation and the clear supernatant was applied to a column (25×800 mm) of ULTROGEL AcA 34 or Aca 44 equilibrated and eluted with the same buffer to remove impurities. The retained haemagglutinating material appeared in a peak eluted by 0.05M.Tris/HCl buffer containing 0.5M NaCl (pH7.2). The fractions from the main peak and having haemagglutinatious properties were pooled and kept frozen or re-precipitated by dialysis against 0.025M Bis-Tris/HCl buffer, pH 7.1 and dissolved in a smaller volume of β-alanine buffer. The solubility is approximately 3.0 mg FHA/ml. The final product thus obtained, either from the Tomaha, BP357 or W28 LPF strain does not contain detectable amount of LPF as measured by CHO cell assay (which was negative at a concentration of 2-3 ug FHA per single well containing 200 ul tissue culture; sensitivity of the test: 1-2 pg LPF per well gives a positive clumping) or by histamine sensitization. The N:NIH-S mice were injected with doses of 50 ug of FHA interperitoneally and challenged 4 days later by intraperitoneal injection of 4 mg histamine hydrochloride. None of them died. The material frozen (at −20 or −40° C.) at acid pH appears stable as judged from its ELISA reactivity and appearance in the SDS-PAGE: It forms prevalently three strong bands in the region of 150-100 kD.

EXAMPLE 2

69 kDa antigen was prepared in accordance with the procedures outlined in published European patent application No. 0162 639. Using either strain BP357 or W28ΔLPF of *B. pertussis*, and immunopurified using the monoclonar antibody BB05—deposited at the Public Health Laboratory Service Centre for Applied Microbiology and Research, Porton Down, Salisbury Wiltshire SP4 OJC United Kingdom, under No 90020103 on 1Feb. 1990.

EXAMPLE 3

Kendrick Test

This was performed according to W. H. O. Requirements for Pertussis Vaccine using outbred NIH-S mice (OLAC, category 3, free of most pathogens including *B. bronchiseptica), weighting* 14-16 g. The antigens, in 0.5 ml volumes, were inoculated intraperitoneally as a mixture, and comprised a top dilution and three three-fold serial dilutions. After two weeks the mice were challenged intracerebrally using the recommended challenge strain 18-323 (−400 $LD_{50}$). The number of survivors in each group was used for calculation of the relative potency in respect to the British Pertussis Reference Vaccine 66/84 using a program of parallel line probit analysis. A comparative test was also performed using an 69 kDa/LPF vaccine. The results are shown in Table 1. In this experiment the 69 kDa protein and FHA originated from the strain BP357.

TABLE 1

| | | SURVIVORS |
|---|---|---|
| 69 kd (μg) | FHA (μg) | |
| 20 | 20 | 13/16 |
| 6.7 | 6.7 | 12/16 |
| 2.2 | 2.2 | 8/16 |
| 0.74 | 0.74 | 8/16 |
| 69 kd (μg) | LPF (ng) | |
| 20 | 100 | 8/16 |
| 6.7 | 33 | 6/16 |
| 2.2 | 11 | 0/16 |
| 0.74 | 3.7 | 1/16 |
| 66/84 | I. U. | |
| Whole cell UK | 0.25 | 9/15 |
| reference | 0.08 | 9/16 |
| vaccine | 0.028 | 2/16 |
| | 0.009 | 1/16 |

This data was computed according to the methodology of parallel line probits analysis. The results are displayed in FIG. 1.

The results clearly show that the 69 kDa/FHA vaccine is more potent than 69 kDa/LPF and at least as, if not more, potent than the whole cell vaccine.

EXAMPLE 4

Combinations and/or individual antigens originating from the strain W28 LPF of *Bordetella pertussis* were used in another Kendrick test. Since in this strain the whole toxin gene has been blocked, the possibility that these preparations were contaminated by LPF is nil. The antigen(s) in 0.5 ml volumes were inoculated intraperitoneally, individually or as mixtures and comprised a top dose and three four-fold dilutions. After two weeks the mice were challenged intracerebrally using a challenge strain 18-323 (ca 400 LD50). The number if survivors in each group was used for the calculation of the relative potency in respect of the British Pertussis Reference Vaccine 66/84 ysing a program of parallel line probit analysis. The British Reference 66/84 was used at top dilution containing 0.5 I.U. and three four-fold serial dilutions. The results are shown in table 2 and FIG. 2.

TABLE 2

| | FHA (ug) | LPF (ng) | SURVIVORS/TOTAL |
|---|---|---|---|
| 69 kDa (ug) | | | |
| 20.0 | — | — | 0/18 |
| 5.0 | — | — | 1/18 |
| 1.25 | — | — | 1/18 |
| 0.325 | — | — | 0/18 |
| 20.0 | — | 100.0 | 8/17 |
| 5.0 | — | 20.0 | 3/17 |
| 1.25 | — | 5.0 | 0/20 |
| 0.325 | — | 1.25 | 0/18 |
| 20.0 | 20.0 | — | 14/18 |
| 5.0 | 5.0 | — | 8/18 |
| 1.25 | 1.25 | — | 3/18 |
| 0.325 | 0.325 | — | 1/18 |
| — | 20.0 | — | 0/17 |
| — | 5.0 | — | 6/18 |
| — | 1.25 | — | 4/18 |
| — | 0.325 | — | 1/17 |
| Whole cell reference 66/84 | | | |
| 0.5 I. U. | | | 16/17 |
| 0.125 | | | 13/18 |
| 0.031 | | | 8/17 |
| 0.008 | | | 0/18 |
| Challenge titration: | | | |
| Challenge dose | | | 0/11 |
| Challenge dose 1/50 | | | 1/10 |
| Challenge dose 1/250 | | | 2/10 |
| Challenge dose 1/1250 | | | 6/9 |

EXAMPLE 5

Subcellular vaccines prepared from *B. pertussis* cultures by various procedures have already been made (BIKEN, TAKEDA, LEDERLE, CONNAUGHT) which apart from impurities may also contain LPF, FHA and up to 10% of the 69 kDa protein. However, none of these subcellular vaccines has shown any reasonable protective potency in the WHO mouse potency assay. If however, a fresh preparation of the 69 kDa protein has been added to these non-protective vaccines, their protective efficacy has been augmented (TABLE 3). As all these mentioned impure preparations were treated by formalin or glutaraldehyde, their protective potency has been damaged. The 69 kDa protein must not be treated by formalin or glutaraldehyde; such forms do not induce sufficient antibodies in mice after intraperitoneal injection as opposed to the antigen before formalin or glutaraldehyde treatment.

TABLE 3

| ANTIGEN | SURVIVAL/TOTAL |
|---|---|
| 69 kDa | |
| 20.0 ug | 1/10 |
| 5.0 ug | 2/10 |
| 1.25 ug | 0/9 |
| 0.325 ug | 0/10 |
| Biken PPP3 | |
| 0.5 U. | 4/9 |
| 0.125 | 2/10 |
| 0.031 | 0/10 |
| 0.008 | 0/10 |
| Connaught lot 17 | |
| 18.5 ug | 6/10 |
| 4.62 | 0/9 |
| 1.16 | 2/10 |
| 0.29 | 0/10 |
| 69 kDa + Biken PPP3 | |
| 20.0 ug + 0.5 U | 8/10 |
| 5.0 ug + 0.125 | 6/9 |
| 0.125 + 0.032 | 4/10 |
| 0.0325 + 0.008 | 1/10 |
| 69 kDa + Connaught lot 17 | |
| 20.0 ug + 18.5 ug | 8/10 |
| 5.0 ug + 4.62 | 5/10 |
| 0.125 + 1.16 | 2/10 |
| 0.0325 + 0.29 | 0/10 |
| Reference 66/84 | |
| 0.5 U | 6/10 |
| 0.125 | 4/10 |
| 0.032 | 3/10 |
| 0.008 | 2/10 |

LD50 was estimated for each antigen (vaccine) separately or in mixtures using probit analysis fitting parallel lines.

| | LD50 and their 95% fiducial limits | |
|---|---|---|
| ANTIGEN | LD50 | 95% fiducial limits |
| 69 kDa | 103.5 ug | 3.4 – 5300 ug |
| Biken PPP3 vaccine | 0.94 U | 0.13 – 10.2 U |
| Connaught | 20.6 ug | 4.6 – 124.7 ug |
| 69 kDa + Biken PPP3 | 2.7 ug + 0.07 U | 1.0-7.1 ug + 0.03-0.18 U |
| 69 kDa + Connaught | 6.1 ug + 5.7 ug | 2.3-18.5 + 2.1-17.1 |
| Whole cell reference 66/84 | 0.14 I.U. | 0.05 – 0.42 I.U. |

| Relative potency of vaccines alone and their combinations with 69 kDa protein | | |
|---|---|---|
| ANTIGEN(S) | RELATIVE POTENCY (dilution factor) | 95% fiducial limits |
| Biken PPP3 and Biken PPP3 + 69 kDa | 10.9 | 3.2-83.3 |
| Connaught and Connaught + 69 kDa | 3.0 | 0.9-12.5 |

The combination Biken PPP3+69 kDa is significantly different at the 1% level from the Biken PPP3 alone. Due to the non graded response to the Connaught vaccine alone the comparison with the combination Connaught+69 kDa is not statistically significant. This vaccine (lot 17) also contained large quantities of free pertussis toxin and was therefore unsuitable for human use.

The invention claimed is:

1. An acellular *pertussis* vaccine comprising a combination of *Bordetella pertussis* antigens, said combination consisting of isolated and purified 69 kDa antigen of *Bordetella pertussis* and isolated and purified filamentous haemagglutinin antigen of *Bordetella pertussis*, wherein the 69 kDa antigen and the filamentous haemagglutinin antigen are present in a ratio of from 1:1 to 1:10, wherein the vaccine is effective in inducing protection in a mammal to subsequent challenge by a virulent strain of *Bordetella pertussis*.

2. The acellular vaccine as claimed in claim 1, wherein the vaccine comprises a pharmaceutically acceptable excipient.

3. The acellular vaccine as claimed in claim 2, wherein the pharmaceutically acceptable excipient is a saline solution.

4. The acellular vaccine as claimed in claim 1, wherein the vaccine does not comprise lymphocytosis promoting factor of *Bordetella pertussis*.

5. The acellular vaccine as claimed in claim 1, wherein the ratio of the 69 kDa antigen to the filamentous haemagglutinin antigen is 1:1.

6. The acellular vaccine as claimed in claim 1, wherein the vaccine comprises an adjuvant.

7. The acellular vaccine as claimed in claim 6, wherein the adjuvant is aluminum hydroxide.

8. The acellular vaccine as claimed in claim 6, wherein the adjuvant is aluminum phosphate.

9. A method of vaccinating a mammal susceptible to *Bordetella pertussis* infection comprising administering to the mammal an acellular *pertussis* vaccine comprising a combination of *Bordetella pertussis* antigens, said combination consisting of isolated and purified 69 kDa antigen of *Bordetella pertussis* and isolated and purified filamentous haemagglutinin antigen of *Bordetella pertussis*, wherein the 69 kDa antigen and the filamentous haemagglutinin antigen are present in a ratio of from 1:1 to 1:10, wherein the vaccine is effective in inducing protection in a mammal to subsequent challenge by a virulent strain of *Bordetella pertussis*.

10. The method as claimed in claim 9, wherein the mammal is a human.

11. The method as claimed in claim 9, wherein the vaccine comprises a pharmaceutically acceptable excipient.

12. The method as claimed in claim 11, wherein the pharmaceutically acceptable excipient is a saline solution.

13. The method as claimed in claim 9, wherein the vaccine does not comprise lymphocytosis promoting factor of *Bordetella pertussis*.

14. The method as claimed in claim 9, wherein the ratio of the 69 kDa antigen to the filamentous haemagglutinin antigen is 1:1.

15. The method as claimed in claim 9, wherein the vaccine comprises an adjuvant.

16. The method as claimed in claim 15, wherein the adjuvant is aluminum hydroxide.

17. The method as claimed in claim 15, wherein the adjuvant is aluminum phosphate.

18. A method of formulating an acellular *pertussis* vaccine comprising (i) a combination of *Bordetella pertussis* antigens, said combination consisting of isolated and purified 69 kDa antigen of *Bordetella pertussis* and isolated and purified filamentous haemagglutinin antigen of *Bordetella pertussis* and (ii) a pharmaceutically acceptable excipient, wherein the 69 kDa antigen and the filamentous haemagglutinin antigen are present in a ratio of from 1:1 to 1:10, wherein the method comprises admixing the pharmaceutically acceptable excipient with the combination of the *Bordetella pertussis* antigens.

19. The method as claimed in claim 18, wherein the pharmaceutically acceptable excipient is a saline solution.

20. The method as claimed in claim 18, wherein the vaccine does not comprise lymphocytosis promoting factor of *Bordetella pertussis.*

21. The method as claimed in claim 18, wherein the ratio of the 69 kDa antigen to the filamentous haemagglutinin antigen is 1:1.

22. The method as claimed in claim 18, wherein the vaccine comprises an adjuvant.

23. The method as claimed in claim 22, where the adjuvant is aluminum hydroxide.

24. The method as claimed in claim 22, wherein the adjuvant is aluminum phosphate.

25. The acellular vaccine as claimed in claim 3, wherein the vaccine comprises an adjuvant.

26. The acellular vaccine as claimed in claim 25, wherein the adjuvant is aluminum phosphate.

27. The method as claimed in claim 12, wherein the vaccine comprises an adjuvant.

28. The method as claimed in claim 27, wherein the adjuvant is aluminum phosphate.

29. The method as claimed in claim 19, wherein the vaccine comprises an adjuvant.

30. The method as claimed in claim 29, wherein the adjuvant is aluminum phosphate.

* * * * *